US Patent 4,076,892 — Fennimore et al. — Feb. 28, 1978

[54] TREATMENT OF PARTICULATE CARBON

[75] Inventors: Jack Fennimore, Welwyn; Gary Ruder, Harlow Essex; Donald Simmonite, Hertford, all of England

[73] Assignee: T. J. Smith & Nephew Limited, Hull, England

[21] Appl. No.: 491,293

[22] Filed: Jul. 24, 1974

[30] Foreign Application Priority Data

Jul. 26, 1973 United Kingdom .............. 35676/73
Jul. 26, 1973 United Kingdom .............. 35677/73

[51] Int. Cl.² .................. A61K 9/30; A61K 9/32; B01D 39/20

[52] U.S. Cl. .................. 428/407; 210/504; 424/31; 424/32; 424/35; 252/426; 427/2; 210/506; 210/DIG. 23; 427/221; 427/222

[58] Field of Search ............. 428/403, 407; 427/221, 427/222; 210/504, 506, DIG. 23; 260/89.5 A, 29.6 H; 427/244, 245; 23/252.5 R; 252/426, 428; 424/10; 128/214 B

[56] References Cited

U.S. PATENT DOCUMENTS

| | | | |
|---|---|---|---|
| 2,040,818 | 5/1936 | Badollet | 210/506 |
| 2,668,151 | 2/1954 | Pedlow et al. | 210/506 |
| 2,984,635 | 5/1961 | Harris | 428/403 |
| 3,109,750 | 11/1963 | Roche | 427/244 |
| 3,238,056 | 3/1966 | Pall et al. | 210/506 |
| 3,443,492 | 5/1969 | Pleass | 427/221 |
| 3,522,346 | 7/1970 | Chang | 23/258.5 R X |
| 3,544,507 | 12/1970 | Lloyd | 428/407 |
| 3,661,620 | 5/1972 | Dekking et al. | 427/221 |
| 3,669,691 | 6/1972 | DeLong et al. | 260/29.6 H |
| 3,681,269 | 8/1972 | Heitz et al. | 260/89.5 A |
| 3,704,786 | 12/1972 | Lerner et al. | 210/504 |
| 3,725,113 | 4/1973 | Chang | 23/258.5 R X |
| 3,802,909 | 4/1974 | Rockett et al. | 427/221 |

FOREIGN PATENT DOCUMENTS

| | | | |
|---|---|---|---|
| 1,156,653 | 7/1969 | United Kingdom | 427/221 |
| 790,636 | 2/1958 | United Kingdom | 427/221 |

Primary Examiner—James R. Hoffman
Assistant Examiner—S. Silverberg
Attorney, Agent, or Firm—Robert L. Goldberg; David G. Conlin

[57] ABSTRACT

Particulate porous absorptive material such as carbon is coated with a biocompatible polymer to give a thin (e.g. 1-10 micron) smooth permeable coating without plugging the pores. The resulting material is free from fines and surface debris and useful for haemoperfusion. Coating is best effected by spraying hot washed carbon granules, free from fines and in rapid movement with a solution of polymer (e.g. polyHEMA) so as to bring about rapid evaporation and a coating weight preferably of up to 20% usually 0.25% to 5%.

3 Claims, 7 Drawing Figures

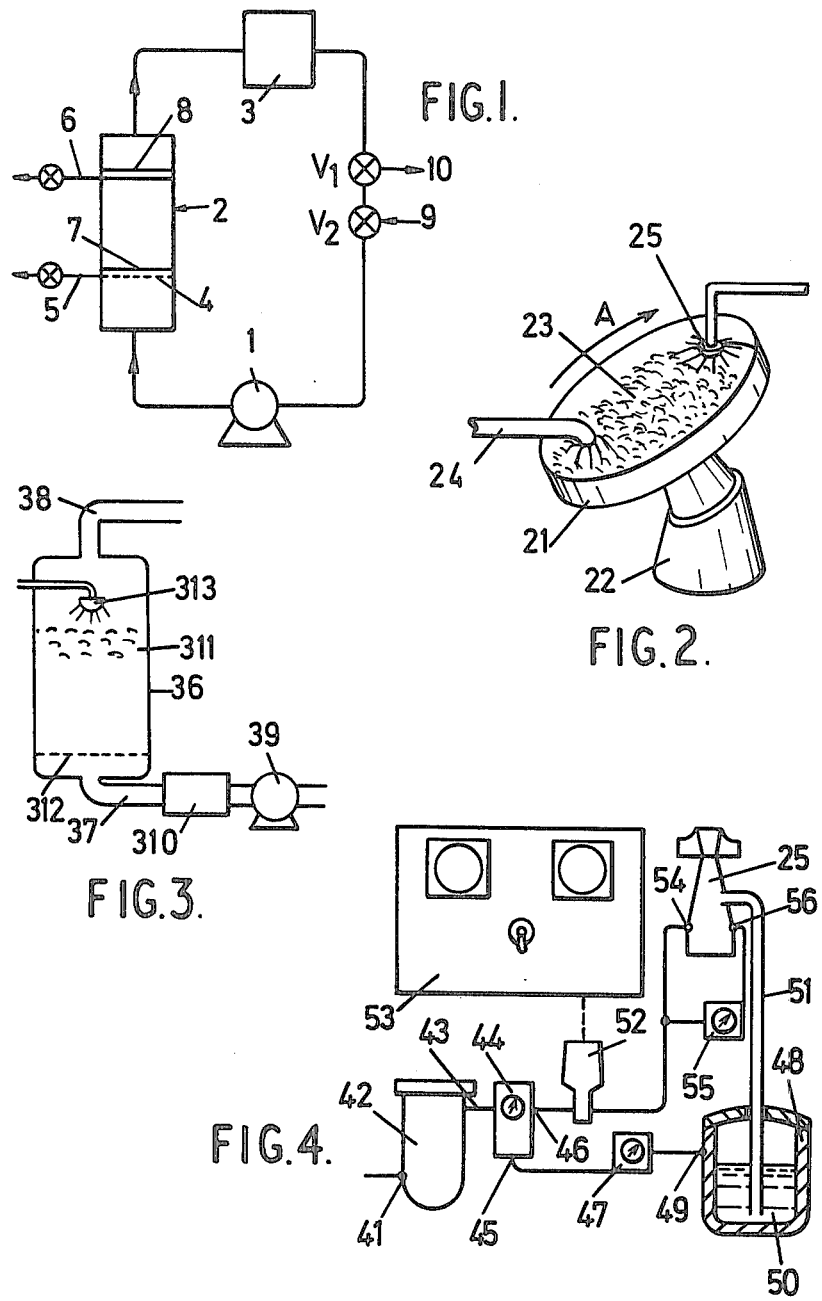

TREATMENT OF PARTICULATE CARBON

BACKGROUND OF THE INVENTION

The present invention relates to the treatment of particulate absorptive material, e.g. porous polystyrene granules but especially absorptive carbon granules. It is particularly useful for treatment of such granules which are low in or free from insoluble impurities and fines. It is especially valuable as a treatment for carbon granules previously washed free of fines and surface debris. The product of this invention, while it has general utility in chemical process engineering, has particular application where purity is essential e.g. in the treatment of food and drink and especially in a medical context.

Particulate carbons of value in the medical field (for example in the detoxification of blood from poisons) are known. However, they have a disadvantage in that they tend to introduce carbon fines or impurities, into the blood stream and may lead to the breakdown of blood cells over rough particle surfaces due to turbulence and more especially platelet adhesion, which can reduce the platelet count by 50% or more.

SUMMARY OF THE INVENTION

The present invention provides a material which alleviates or overcomes these problems, and in one aspect consists of a particulate porous absorptive material, especially carbon, the particles of which are provided with a protective permeable layer over, or at, the particle surface of a bio-compatible polymer, such layer hindering mechanical breakdown of the particles and providing a smooth permeable particle surface without plugging the pores of the material. The layer is usually from 1 - 10 microns thick. Preferably the coating is formed by evaporation of a solution of the polymer. The particulate material is preferably carbon, (Sutcliffe Speakman grade 610, 5-10 mesh, prepared from coconut shell is of especial value) but polystyrene-based granules, especially those available from Rohm and Haas under the trade designations XAD2, XAD4 and XAD7 can also be used. Particle sizes for carbon or other absorbents are widely variable but below 40 mesh is preferred e.g. 5-10, 18-40, 10-16, 16-30 all being possible.

The biocompatible polymers may be, for example, poly (hydroxyethylmethacrylate) referred to hereafter as polyHEMA, cellulose acetate, polyurethane, silicone, or polyamide.

The polymer may be present in amounts up to 20% of the total weight of the absorptive material. Preferably it is present in amounts in 0.25 to 5%, and for example in amounts of about 3%. It is desirable to use as little as is consonant with a good coating.

The absorptive particulate material such as carbon to be used in the process may itself be prepared by a method of treatment wherein a bed of the particulate material is subjected to an upwardly flowing current of a treatment liquid at such a rate as to agitate individual particles and remove fines from among them in the current of liquid, while preserving the integrity of the bed, whereby additional fines are not produced by attrition. This washing method also envisages location of a concentration of insoluble impurities at the top and/or at the bottom of the treatment bed for subsequent removal, since such insoluble impurities, depending on their size, shape, specific gravity, the nature of treatment liquid and rate of flow of the treatment liquid will either fall to the bottom of the treatment bed or rise to the top. Such a treatment liquid may itself be used to impregnate the material with a biocompatible polymer, prior to coating according to the present invention.

The present invention also envisages a method of treatment of porous particulate absorptive material such as carbon where a heated mass of particles, the individual members of which are caused or allowed to adopt relative motion, are sprayed with a solution of a biocompatible polymer in an amount such that the solvent evaporates leaving a coating over, or at, each particle surface. Such particles themselves may be impregnated e.g. with the same or a different biocompatible polymer.

The particles in the mass may be put in rapid relative motion by tumbling over an inclined surface, for instance an inclined rotary pan, or by being provided as a violently agitated turbulent spray or curtain e.g. a boiling bed. In either case the mass of particles is most conveniently maintained in a heated condition by a stream of heated air.

The solution used for spraying the particles may be for instance an aqueous ethanolic solution of polyHEMA, or a toluene solution of a silicone resin. In the first instance at least, the proportion of water to ethanol by volume is preferably from 10:90 to pure ethanol, e.g. about 5:95.

It is possible to arrange for the sprayed coating to contain a proportion of micronised (i.e. very finely divided) NaCl or other watersoluble salt, so that after subsequent leaching the permeability of the polymer layer is improved.

A suitable temperature to which the particulate material may be heated prior to spraying is from 30 to 100° C and most preferably from 35° to 70° C such as about 40° C. Optionally the particulate material, after coating, may be dried more thoroughly by heating it at a higher temperature e.g. from 100° to 150° C such as about 120° C.

In a modification of the above method, a solution of a monomer, which polymerises in contact with the heated mass of particles, could be used; this may however suffer from the disadvantage that a catalyst is usually necessary to polymerise the monomer readily, and this catalyst could contaminate the material.

As described above, a further optional feature of the method involves dipping the carbon particles in a suitable impregnant, to modify their properties, prior to coating. This can be a polymer solution, or other impregnant. The method of washing described above provides a simple manner of impregnating the carbon particles.

The present invention also provides apparatus for carrying out the above method of coating the particles, comprising means for holding a mass of porous absorptive particulate material such as carbon while causing or allowing relative motion of the individual particles; a spray head for supplying a solution of biocompatible polymer to said mass; and means to heat the mass.

Such apparatus can comprise a vessel for providing a violently agitated turbulent spray or motion, such as a fluidised bed vessel, or a rotary inclined pan, as a suitable means for holding the mass of particulate carbon.

Preferably means for heating the mass include hot air supply means, such as may be used for agitating the particles, or for playing on the particles in the rotating pan, respectively.

The present invention also provides a method of detoxification of blood using absorptive porous granular material, such as carbon, coated as described above.

BRIEF DESCRIPTION OF THE DRAWING

The invention will now be further described with reference to the accompanying drawings in which:

FIG. 1 is a diagram of a vessel and liquid flow circuit for carrying out a washing treatment of particulate carbon;

FIG. 2 is a diagrammatic view of one form of equipment used for coating particulate carbon;

FIG. 3 is a diagrammatic section of another form of equipment for this purpose;

FIG. 4 is a schematic diagram of spray equipment which can be used in coating particulate carbon.

In FIG. 1 a pump 1 passes liquid into the base of a treatment vessel 2 from which it leaves at the top and passes through a $3\mu$ filter 3 and via valves $V_1$ and $V_2$ back to the pump 1.

Figure 5:
FIGS. 5, 6 and 7 are photomicrographs of carbon granules.

Vessel 2 has a transverse gauze 4 or like perforate support for supporting a bed of the particulate carbon to be treated, and outlets 5 and 6 in the form of valved pipes.

In use a suitable carbon is placed on the gauze 4 and the treatment liquid which is typically 50:50 aqueous ethanol is pumped around the circuit by pump 1 at such a rate that particles are agitated (i.e. they rotate and move about their axes in relation to each other) but they do not translate in relation to one another to such an extent as to destroy the integrity of the bed.

Initially, fines are washed through the bed of agitated particles using a high liquid flow rate, and accumulate in the filter 3. Heavy particulate impurities, (for example mineral impurities such as gravel, sand or pieces of metal) depending on their size, shape, density, the nature of the liquid and the rate of flow, move downwards through the bed and eventually accumulate, e.g. as a layer 7, on the gauze 4. Lighter impurities such as wood, ash or bone, again depending on the foregoing considerations, move upwards through the bed and eventually accumulate, e.g. as a layer 8, on top of the essentially quiet bed of individually agitated particles.

Valves $V_1$ and $V_2$ are then operated so that water enters at 9, progressively washes out the aqueous alcohol from the column, and leaves at 10 carrying the aqueous alcohol. This is typically carried out at a lower flow rate than the initial stage. Optionally at this stage an additional wash with hot (60° – 70° C) water will improve results.

Layers 7 and 8 are thereafter drained off laterally through the pipes 5 and 6 respectively, while the pump is still operating, top layer 8 usually being drained off before lower layer 7. Thereafter, the pump is stopped and the slurry of carbon purified from fines and contaminants is drained off at 5.

In FIG. 2 an inclined 16-inch stainless coating pan 21, rotary in the direction of arrow A and mounted on stand 22, contains 3 kg. of carbon granules 23 freed from fines and impurities and optionally impregnated with a biocompatible polymer, or other impregnant as described above. These granules are heated to 45° C by hot air at 55° C conveyed through duct 24 at 20 cubic ft./min and playing on the pan. The heated granules are intermittently or continuously sprayed by spray head 25, that is to say when they are in rapid tumbling motion, with a fine spray of a 4% by weight solution of polyHEMA polymer in 5:95 aqueous ethanol, to a total uptake of 3% by weight polymer. Since the thermal mass of hot carbon is much greater than that of the impinging spray the solvent rapidly evaporates and the polymer forms a layer over, or in any case essentially at the surface of, the carbon particles which layer in addition to being biocompatible because of the nature of the polymer also binds the particles against abrasion (and thus re-formation of the fines) and gives a smooth surface which would prevent platelet adhesion and breakdown of blood, or similar degradation of a like environment-sensitive liquid, flowing past it.

Figure 6:
Figure 7:

The product can be distinguished from carbon merely impregnated with solutions by dipping. In such carbons, where the solutes are small inorganic molecules, the impregnation is essentially uniform throughout the particles. Where a solution of polymer is proposed in the prior art, for instance as in French Pat. No. 71.03838, effective impregnation is also much deeper than in the present invention, since in that earlier process the particles are contacted for a relatively long time (typically two minutes) with liquid, prior to precipitation from that liquid within the pores. Accordingly, the particles must contain precipitate throughout. On the other hand, the process of the present invention coats the particles over, or at, the surface only. The use of a large body of carbon granules and a fine spray so that solvent rapidly evaporates leaving the polymer at, and in, the surface layer only ensures that the pores remain substantially unplugged, as shown in FIGS. 6 and 7. Moreover, where polymer impregnation is followed by a spray treatment according to the invention the product is distinguished, under electron microscopy, from either the merely impregnated or the merely sprayed product.

While the Applicants do not intend to be bound by any statement regarding the theoretical basis of their invention as described herein, it is believed that an impregnation process alone, while possibly coating a greater surface area (since it lines the pores) yields a carbon that still possesses a rough and cracked surface while being friable and liable to break up into small particles. The spray process appears to avoid this and to give a smooth surfaced particle free from surface debris while still giving a carbon of acceptable absorption rate, usually governed by the permeability of the thin essentially uniform layer which is typically from $10^{-7}$ to $10^{-6}$ cm$^2$/sec.

EXAMPLE 1

The absorption of materials onto carbon 610 was studied using a batch system. A known weight of washed and dried carbon 610 either untreated, or treated as itemised below, was placed in a known volume of a solution of paracetamol. This was placed in a shaking water bath set at 37° C. Samples were removed from the test solutions for analysis after 4 hours. Knowledge of the initial concentration and solution volume of the adsorbate and the mass of adsorbent used, allowed the amount adsorbed to be calculated. Results were as follows:

| | |
|---|---|
| Uncoated carbon | 250 mg/gm. |
| 2% Impregnated (polyHEMA) | 235 mg/gm. |
| 4% Impregnated (polyHEMA) | 225 mg/gm. |
| 2% Spray coated (polyHEMA) | 220 mg/gm. |
| 4% Spray coated (polyHEMA) | 195 mg/gm. |

Thus, spray coated material according to the present invention has under these conditions absorption characteristics not substantially inferior to those of uncoated, or of impregnated, material.

EXAMPLE 2

Spray coated materials show advantages in that there is a smaller loss of fine particles into the liquid stream. This was measured by taking various carbons, either untreated or treated, successively: Unwashed, uncoated; Washed, uncoated; 0% dip, 2% spray; 0% dip, 4% spray; 1.89% dip, 0% spray; 3.75% dip, 0% spray; and 2.82% dip, 3.07% spray.

A column was filled with 315 g. of carbon and a total of 20 liters of nominal 1% saline passed through the column, one liter at a time in each direction, at 1750 ml./min. Coulter counter analysis was effected on each sample, to determine the number of particles larger than $2\mu$ and larger than $5\mu$. Typical results were as follows:

| Vol through column (l) | Mean count/ml minus blank $\geq 2~\mu m$ | | | | | | |
|---|---|---|---|---|---|---|---|
| | Unwashed uncoated | Washed uncoated | 0% dip 2% spray | 0% dip 4% spray | 1.89% dip 0% spray | 3.75% dip 0% spray | 3% dip 3% spray |
| 1 | 1,396,700 | 40,655 | 9,972 | 9,505 | 115,062 | 34,662 | 11,305 |
| 3 | 152,764 | 6,267 | 1,188 | 780 | 8,986 | 2,412 | 1,636 |
| 6 | 27,364 | 2,319 | 476 | 391 | 7,145 | 1,291 | 692 |
| 12 | 15,514 | 791 | 192 | 184 | 6,609 | 1,135 | 953 |

| Vol through column (l) | Mean count/ml minus blank $\geq 5~\mu m$ | | | | | | |
|---|---|---|---|---|---|---|---|
| | Unwashed uncoated | Washed uncoated | 0% dip 2% spray | 0% dip 4% spray | 1.89% dip 0% spray | 3.75% dip 0% spray | 3% dip 3% spray |
| 1 | 15,988 | 524 | 558 | 282 | 2,220 | 470 | 429 |
| 3 | 378 | 62 | 93 | 61 | 412 | 192 | 76 |
| 6 | 83 | 69 | 39 | 51 | 249 | 107 | 44 |
| 12 | 38 | 29 | 30 | 19 | 135 | 70 | 78 |

From graphing the results obtained for all twenty readings, it is apparent that not only does spray-coating give improved results over impregnation, but also that even after twenty reversals spraycoated particles are still improving whereas dipped particles have reached a constant (and higher) value.

FIG. 3 shows an alternative manner of obtaining a similar coating. A vessel 36 has an air inlet 37 at the base and outlet 38 at the top. Inlet 37 is fed with hot air by pump 39 and heater 310 and this air serves to violently agitate a bed of carbon 311 supported on gauze or like support 312. A fine spray of a polymer solution is fed above the bed at 313, solvent vapours being rapidly blown out with the air at outlet 38. Again, short contact of a small thermal mass of solvent with an agitated high thermal mass of hot carbon leads to effective surface deposition of polymer.

FIG. 4 shows a typical arrangement for supplying the spray head 25 (FIG. 2).

Air at 40–80 pounds per square inch (p.s.i.) is fed at 41 into a carbon filter 42, leaving at 43 and passing into reducing valve 44 with outlets 45 and 46 at a pressure of 35 p.s.i. Further reducing valve 47 reduces the air leaving outlet 45 and entering the upper part of pressure vessel 48 at inlet 49 to 3 p.s.i. This pressure vessel contains 1500 ml. of a 4% w/v polyHEMA solution in its lower part at 50, and this solution is forced by the 3 p.s.i. air through duct 51 pressure to spray head 25.

Air leaving outlet 46 passes through on-off solenoid valve 52 controlled by electronic timer 53 to inlet 54 in the spray head, as the main supply of air (at 35 p.s.i.) carrying the spray. However, further reducing valve 55 is provided in a line 56 to give a 10 p.s.i. supply of air to atomise the liquid arriving through duct 51.

Typically, 7-second sprays separated by 53-second drying times have been found useful, hot air heating being continued until five minutes after spraying is complete.

Various modifications may be made within the scope of the invention. For instance, it is conceivable to spray carbon held in a shaker vessel, or to spray the heated carbon with a solution of polymerisable monomer so as to effect polymerisation rapidly in situ on the carbon surface.

The product of the method can usefully be used with the column for detoxification of blood shown in our copending application 35678/73.

Thus another aspect of the invention consists in a particulate porous absorptive material as described above held within a detoxification column of biocompatible material primed with a sterile degassed liquid.

FIGS. 5, 6 and 7 show the effect of the coating process. In each case the same (900x) magnification is used. FIG. 5 shows the surface of an unwashed uncoated carbon granule carrying a large amount of carbon fines as loose debris.

FIG. 6 shows the surface of a washed carbon granule with a 2% by weight coating of polyHEMA, and shows a smooth undulating surface.

FIG. 7 shows a section through granule as in FIG. 6. The surface polyHEMA membrane or skin is about $5\mu$ thick and bridges the pores without penetrating them or plugging them.

What we claim is:

1. A particulate absorbtive material comprising absorbtive carbon granules, said granules being coated at their surface only with a protective permeable layer of a polymer which is compatible with blood selected from the group consisting of poly (hydroxyethylmethacrylate), cellulose acetate, polyurethane, silicone, and polyamide, said layer being formed by spray coating, said layer being from about 1 to 10 microns in thickness and present in an amount of up to about 20% by weight of the total material, and said layer having a smooth permeable surface and hindering mechanical breakdown of the particles without impregnation and consequent plugging of the pores of the absorbtive granules by the polymeric layer.

2. A particulate material as claimed in claim 1, wherein the polymer is a poly (hydroxyethylmethacrylate).

3. A particulate material as claimed in claim 1 wherein the polymer is present in an amount of from 0.25 to 5% by weight of the total material.

* * * * *

UNITED STATES PATENT AND TRADEMARK OFFICE
Certificate

Patent No. 4,076,892      Patented February 28, 1978

Jack Fennimore, Gary Ruder and Donald Simmonite

Application having been made by Jack Fennimore, Gary Ruder and Donald Simmonite, the inventors named in the patent above identified, and T. J. Smith & Nephew Limited, Yorkshire, England, a British Company, the assignee, for the issuance of a certificate under the provisions of Title 35, Section 256, of the United States Code, deleting the name of Gary Ruder as a joint inventor, and a showing and proof of facts satisfying the requirements of the said section having been submitted, it is this 6th day of May 1980, certified that the name of the said Gary Ruder is hereby deleted from the said patent as a joint inventor with the said Jack Fennimore and Donald Simmonite.

FRED W. SHERLING,
*Associate Solicitor.*